(12) United States Patent
Yin et al.

(10) Patent No.: US 12,721,321 B2
(45) Date of Patent: Sep. 1, 2026

(54) METHOD AND SYSTEM FOR MONITORING ABNORMAL STATE OF SWINES BASED ON EDGE COMPUTING

(71) Applicant: Northeast Agricultural University, Harbin (CN)

(72) Inventors: Yanling Yin, Harbin (CN); Weizheng Shen, Harbin (CN); Baisheng Dai, Harbin (CN); Yu Zhang, Harbin (CN); Xiaoli Wei, Harbin (CN); Meng Gao, Harbin (CN); Yan Wang, Harbin (CN); Xiao Fu, Harbin (CN); Xinjie Wang, Harbin (CN); Xin Dai, Harbin (CN)

(73) Assignee: NORTHEAST AGRICULTURAL UNIVERSITY, Harbin (CN)

( * ) Notice: Subject to any disclaimer, the term of this patent is extended or adjusted under 35 U.S.C. 154(b) by 43 days.

(21) Appl. No.: 18/921,643

(22) Filed: Oct. 21, 2024

(65) Prior Publication Data

US 2025/0134072 A1 May 1, 2025

(30) Foreign Application Priority Data

Oct. 27, 2023 (CN) ......................... 202311415297.3

(51) Int. Cl.
*A01K 29/00* (2006.01)
*G06N 20/20* (2019.01)
*G16H 40/67* (2018.01)

(52) U.S. Cl.
CPC ........... *A01K 29/005* (2013.01); *G06N 20/20* (2019.01); *G16H 40/67* (2018.01)

(58) Field of Classification Search
CPC ...... A01K 29/005; G06N 20/20; G16H 40/67; G10L 17/02; G10L 17/04; G10L 17/18; G10L 17/26; H04L 67/125
See application file for complete search history.

(56) References Cited

U.S. PATENT DOCUMENTS

2009/0312660 A1 12/2009 Guarino et al.
2021/0298272 A1* 9/2021 Sarzen .................... G10L 17/26
(Continued)

FOREIGN PATENT DOCUMENTS

CN 108198562 A 6/2018
CN 109493874 A 3/2019
(Continued)

OTHER PUBLICATIONS

S. Adavanne, A. Politis, J. Nikunen and T. Virtanen, "Sound Event Localization and Detection of Overlapping Sources Using Convolutional Recurrent Neural Networks," in IEEE Journal of Selected Topics in Signal Processing, vol. 13, No. 1, pp. 34-48, Mar. 2019 (Year: 2019).*
(Continued)

*Primary Examiner* — Quan Zhen Wang
*Assistant Examiner* — Rajsheed O Black-Childress
(74) *Attorney, Agent, or Firm* — Pilloff Passino & Cosenza LLP; Rachel Pilloff; Sean Passino

(57) ABSTRACT

A method and a system for monitoring abnormal state of swines based on edge computing are provided, including a data acquisition and processing module, an edge computing gateway, a cloud server and a client, where the data acquisition and processing module includes a microphone array, a digital signal processing module, a power amplification module, a power supply module and a communication module; the microphone array is used to acquire and store audio data collected in the pigsty; after being processed by the data processing module, the audio data is transmitted to the edge computing gateway through the communication module; the edge computing gateway identifies and locates the abnormal sound in the pigsty, and sends the result to the cloud server; the cloud server stores the data, establishes an early warning model of the swine abnormal state, and sends
(Continued)

the early warning information to mobile phone or computer client.

8 Claims, 2 Drawing Sheets

(56) References Cited

U.S. PATENT DOCUMENTS

| | | | | |
|---|---|---|---|---|
| 2022/0007618 | A1* | 1/2022 | Berckmans | A01K 29/005 |
| 2022/0030371 | A1 | 1/2022 | Taghizadeh et al. | |

FOREIGN PATENT DOCUMENTS

| | | | |
|---|---|---|---|
| CN | 109817227 | A | 5/2019 |
| CN | 111860203 | A | 10/2020 |
| CN | 112164408 | A | 1/2021 |
| CN | 113661538 | A | 11/2021 |
| CN | 115457966 | A | 12/2022 |
| CN | 115810365 | A | 3/2023 |
| CN | 116034904 | A | 5/2023 |
| CN | 116205595 | A | 6/2023 |
| KR | 102540175 | B1 | 6/2023 |
| KR | 102582506 | B1 | 9/2023 |

OTHER PUBLICATIONS

Shen Mingxia et al., Current Situation and Development Trend of Pig Automated Farming Equipment Application, Journal of Agricultural Machinery, date of issue: Dec. 31, 2022, p. 1-12. Claims involved: 1-10.

Yin Cao et al., “Two-Stage Sound Event Localization and Detection Using Intensity Vector and Generalized Cross-Correlation,” Detection and Classification of Acoustic Scenes and Events, Jan. 2019.

Yanling Yin et al., “An investigation of fusion strategies for boosting pig cough sound recognition,” Computers and Electronics in Agriculture, Jan. 2023, 205, 107645.

First Office Action for China Application No. 202311415297.3, mailed Mar. 12, 2024.

First search Report dated Mar. 8, 2024, in SIPO application No. 202311415297.3.

Notification to Grant Patent Right for Invention dated May 20, 2024, in SIPO application No. 202311415297.3.

Supplementary search dated May 13, 2024, in SIPO application No. 202311415297.3.

* cited by examiner

METHOD AND SYSTEM FOR MONITORING ABNORMAL STATE OF SWINES BASED ON EDGE COMPUTING

CROSS-REFERENCE TO RELATED APPLICATIONS

This application claims priority to Chinese Patent Application No. 202311415297.3, filed on Oct. 27, 2023, the contents of which are hereby incorporated by reference.

TECHNICAL FIELD

The disclosure belongs to the field of voice signal processing, and in particular to a method and a system for monitoring abnormal state of swines based on edge computing.

BACKGROUND

Respiratory diseases are one of the three systemic diseases that affect the healthy breeding of swines in China and restrict the development of swine industry in China, and are also common systemic diseases in large-scale farms. Porcine respiratory diseases may occur all year round, with the highest incidence rate, usually in a range of 30-70%, in late autumn, winter and spring, and the mortality rate is 10-30%. Porcine respiratory diseases mainly occur in the late stage of conservation and the growth and fattening period, and the incidence rate is 30-50%. For fattening swines, respiratory diseases may easily lead to the decrease of swine feed intake, slow growth rate and postponed slaughter time by 10-25 days. Respiratory diseases are more harmful to weaned swines, which may lead to higher mortality if not treated in time. Because of intensive farming mode, respiratory diseases are easy to spread. If one swine suffers from respiratory diseases but is not found in time, the swine will easily infect the whole population, thus increasing the loss of the swine farm.

Meanwhile, for large-scale swine breeding, due to the increase of feeding density, the competition for food/space resources and the increase of the number of mixed groups have led to frequent fighting, tail biting and ear biting. If not stopped in time, it may lead to vicious behaviors such as swine biting. Moreover, the physical injury caused by biting may lead to further infection and other diseases if not treated in time, which will seriously affect the health of swines and even the production performance of the whole swine herd. Timely detection of the abnormal state of swines and taking targeted measures to prevent its large-scale outbreak are important problems that need to be solved urgently in the process of swine breeding, and the key to research and break through these problems is the monitoring and early warning of the abnormal state of swines. At present, the monitoring of abnormal state of swines in large-scale swine farms is still mainly by manual inspection, which commonly includes an irregular observation method and fails to continuously monitor the population in real time. By manual inspection, it is especially difficult to find abnormal swines at night and prone to missed inspection. Moreover, manual inspection may cause cross-infection between humans and swines and stress reaction of swines. Monitoring of abnormal state of swines in pigsty by audio monitoring has the advantages of non-contact, objectivity, accuracy and good real-time, which may realize healthy and intelligent management of large-scale swine farms.

The technical schemes in the prior art have some defects such as low accuracy of abnormal sound recognition, lack of positioning function, fuzzy positioning of abnormal sound, etc., while audio data transmission relying on Wireless Fidelity (WiFi) has the problem of packet loss, and running the algorithm on an ARM board is inefficient in execution. Therefore, a new method and a system for monitoring abnormal state of swines are urgently needed.

SUMMARY

The objective of the present disclosure is to provide a method and a system for monitoring abnormal state of swines based on edge computing, so as to solve the problems existing in the prior art.

In order to achieve the above objective, the present disclosure provides a method for monitoring abnormal state of swines based on edge computing, including:

- collecting and preprocessing audio information through a microphone array, where the audio information is a first-order ambisonics signal, including omnidirectional signals, X-direction signals, Y-direction signals and Z-direction signals;
- performing feature extraction on preprocessed audio information to obtain feature parameters, and performing standard normalization processing on the feature parameters, where the feature parameters include amplitude spectrogram, decibel amplitude spectrogram and phase spectrogram;
- constructing an abnormal sound detection model and an abnormal sound positioning model, constructing a training set, training the abnormal sound detection model and the abnormal sound positioning model based on the training set, and obtaining a classification result and a positioning result of an abnormal sound based on processed feature parameters, the abnormal sound detection model and the abnormal sound positioning model; and
- constructing an early warning model of swine abnormal state, obtaining an abnormal state based on the classification result and the early warning model of the swine abnormal state, counting frequencies of different abnormal states, generating early warning information based on the frequencies and the positioning result, and sending the early warning information to a client, so as to realize monitoring of the swine abnormal state.

Optionally, a preprocessing process includes: performing amplification processing on the audio information, truncating and caching the audio information after the amplification processing to obtain cached data, and performing filtering and denoising processing on the cached data.

Optionally, a training process of the abnormal sound detection model and the abnormal sound positioning model includes:

- collecting clear different sound signals in different pigsties with no superposition of other sound;
- sending pseudorandom sequences by point sound source in different pigsty scenes, and receiving the pseudorandom sequences by microphones, and performing correlation operation on the pseudorandom sequences at a receiving end and a sending end to obtain impulse response in a corresponding scene;
- collecting environmental noises in the different pigsties, wherein the environmental noises refer to background noises; and
- after performing convolution operation on different sound signals and different impulse responses, superimposing the background noises with different energies to obtain a noisy signal set comprising multiple signal-to-noise ratios, and using the noisy signal set as the training set, and training the abnormal sound detection model and the abnormal sound positioning model based on the training set.

Optionally, the abnormal sound detection model uses sigmoid activation function, binary cross entropy as loss function, the abnormal sound positioning model uses linear activation function and average absolute error as loss function.

Optionally, a process of obtaining the classification result and the positioning result of the abnormal sound includes:

inputting the amplitude spectrogram into the abnormal sound detection model to obtain a multi-channel classification result, and performing ensemble learning on the multi-channel classification result to obtain the classification result of the abnormal sound; and judging whether the abnormal sound is in an active state by using the classification result as a mask, and if the abnormal sound is in the active state, inputting the decibel amplitude spectrogram and the phase spectrogram into the abnormal sound positioning model to obtain a multi-channel prediction result, and performing ensemble learning on the multi-channel pre-prediction result to obtain the positioning result of the abnormal sound.

In order to solve the problems in the prior art, the present disclosure also provides a system for monitoring abnormal state of swines based on edge computing, including:

a data acquisition and processing module, an edge computing gateway, a cloud server and a client;

the data acquisition and processing module is used for acquiring an audio signal and processing the audio signal;

the edge computing gateway is used for analyzing an abnormal sound according to processed audio signal, and transmitting analysis results to the cloud server, where the analysis results include a classification result and a positioning result; and the cloud server is used for constructing an early warning model of swine abnormal state, obtaining early warning information based on the analysis results and the early warning model of the swine abnormal state, and transmitting the early warning information to the client.

Optionally, the data acquisition and processing module includes a microphone array, a digital signal processing module, a power amplification module, a power supply module and a communication module;

where the microphone array includes a plurality of directional microphones, a number of the microphones is not less than four, and the microphones are used for collecting audio data, where the audio data includes a multi-channel synchronous audio signal, and collected multi-channel audio signal is encoded and converted into a first-order ambisonics signal;

the power amplification module is used for performing amplification processing on the audio data;

the digital signal processing module adopts a field programmable gate array (FPGA) module, used for extracting feature parameters after the amplification processing on the audio data and transmitting the feature parameters to the edge computing gateway through the communication module; and the power supply module is used for supplying power to the microphone array, the digital signal processing module, the power amplification module and the communication module.

Optionally, the edge computing gateway includes an abnormal sound detection model and an abnormal sound positioning model, both of the abnormal sound detection model and the abnormal sound positioning model include a depth feature extraction layer, a plurality of BiLSTM or BiGRU layers, a full connection layer and an activation layer.

Optionally, the depth feature extraction layer includes a plurality of convolution layers, batch normalization layers, activation function ReLu, pooling layers and Dropout.

Optionally, the early warning information obtained by the early warning model of the swine abnormal state includes several early warning states, frequencies of abnormal sounds and position information of the abnormal sounds.

The disclosure has the following technical effects.

The disclosure provides a method and a system for monitoring abnormal state of swines based on edge computing, which greatly relieve the pressure of network bandwidth and cloud servers through the edge computing gateway, and reduce the time delay and computing energy consumption. According to the disclosure, the first-order ambisonics signal is collected by the microphone array, so that the abnormal sound in the pigsty may be recognized and the abnormal swines may be located; ensemble learning through multiple microphones may effectively improve the accuracy of target sound recognition. The FPGA module adopted in the disclosure may quickly process parallel multi-channel signals and improve the calculation speed; signal feature parameters are extracted from the FPGA module at the same time, and the signal feature parameters are sent to the edge computing gateway through the network, thus greatly reducing the data volume, reducing the transmission of data, improving the transmission efficiency and reducing the transmission delay. The abnormal sound detection model and the abnormal sound positioning model adopted by the disclosure may effectively improve the recognition accuracy and positioning accuracy of the target sound signal by extracting the depth feature and adding the time series classification model through the convolutional neural network, and meanwhile, the stability and generalization ability of the model may be effectively improved through ensemble learning. Furthermore, the disclosure defines the early warning model of abnormal state of swines, and provides a reliable early warning scheme and intelligent management mode for healthy breeding of swines.

BRIEF DESCRIPTION OF THE DRAWINGS

The accompanying drawings, which constitute a part of this application, are used to provide a further understanding of this application. The illustrative examples and descriptions of this application are used to explain this application, and do not constitute an improper limitation of this application. In the attached drawings.

DETAILED DESCRIPTION OF THE EMBODIMENTS

It should be noted that the embodiments in this application and the features in the embodiments may be combined with each other without conflict. The present application will be described in detail with reference to the attached drawings and examples.

It should be noted that the steps shown in the flowchart of the drawings may be executed in a computer system such as a set of computer-executable instructions, and although the logical order is shown in the flowchart, in some cases, the steps shown or described may be executed in a different order from here.

Embodiment 1

Figure 1:
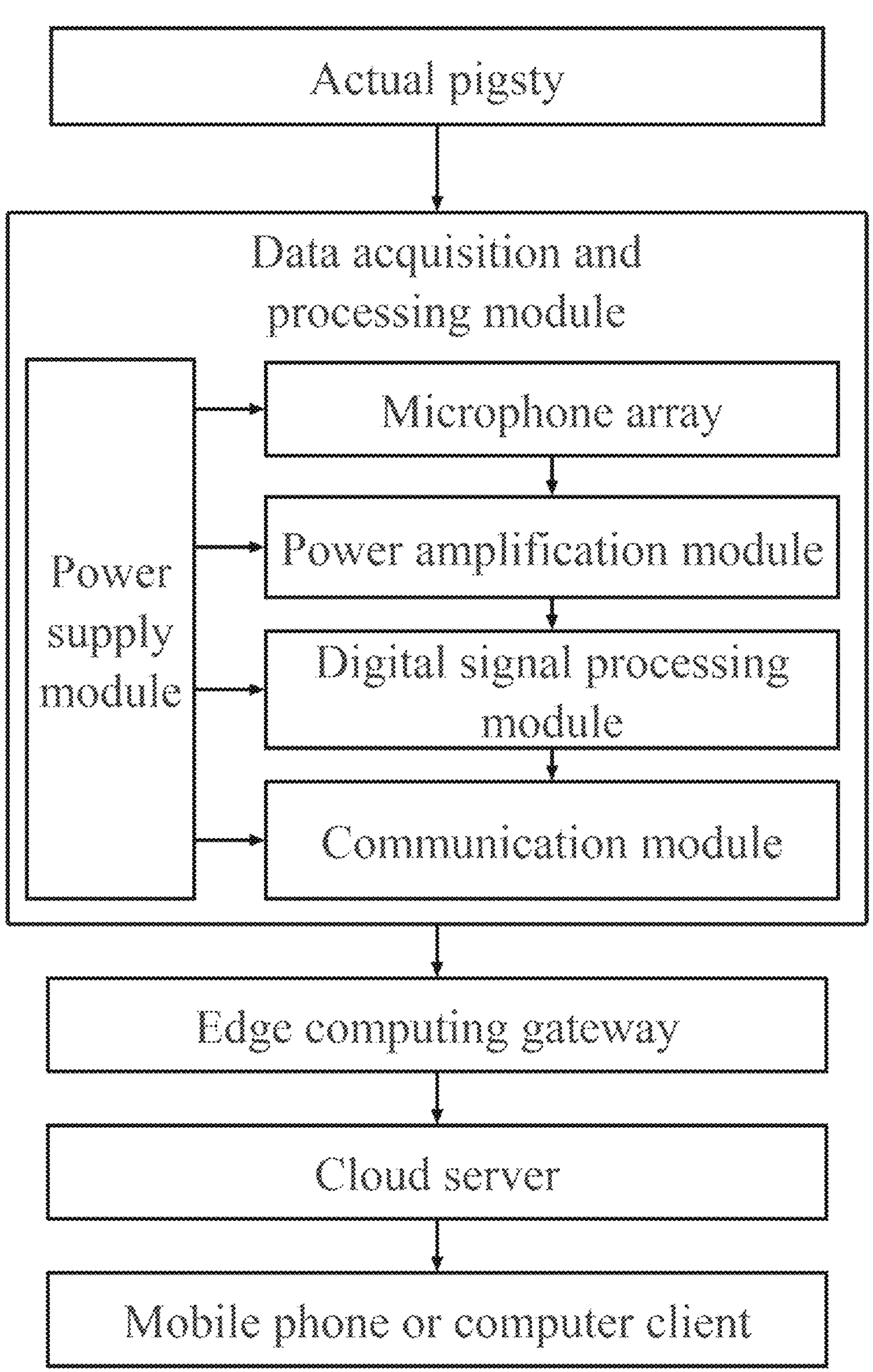
FIG. 1 is a schematic diagram of a method and a system for monitoring abnormal state of swines based on edge computing in an embodiment of the present disclosure.
Figure 2:
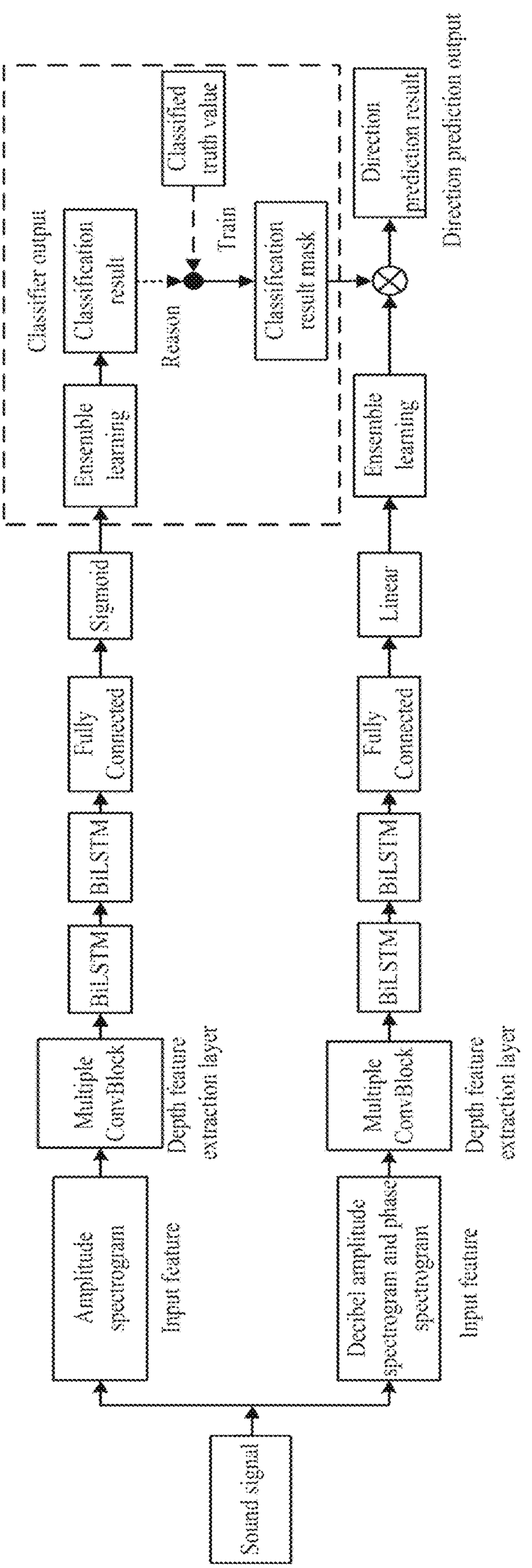
FIG. 2 is a schematic diagram of an abnormal sound detection model and an abnormal sound positioning model in an embodiment of the present disclosure.

As shown in FIG. 1-FIG. 2, in this embodiment, a method and system for monitoring abnormal state of swines based on edge computing are provided, including:

a data acquisition and processing module, an edge computing gateway, a cloud server and a client, where the data acquisition and processing module includes a microphone array, a digital signal processing module, a power amplification module, a power supply module and a communication module, where the power supply module supplies power to the microphone array, the digital signal processing module, the power amplification module and the communication module.

The microphone array includes four directional microphones. The microphone array is arranged in the pigsty where it is suitable for installation and will not be collided by swines, such as at the entrance position or the center position of the pigsty more than 2 meters above the ground. The signals obtained by the microphone array are first-order ambisonics FOA signals, which are W omnidirectional signals, X directional signals, Y directional signals and Z directional signals respectively. Microphone array transmits the collected multi-channel synchronous audio signals amplified by power amplification module to digital signal processing module. The digital signal processing module is a field programmable gate array FPGA module, which intercepts and caches the W, X, Y and Z audio signals collected by the microphone array. The cached data is filtered by band-pass filter and denoised by wavelet, and the frequency range of the band-pass filter is 200 Hz-16 kHz. Feature parameters are extracted from the processed data, where the feature parameters include amplitude spectrogram, decibel amplitude spectrogram and phase spectrogram; the amplitude spectrogram is to take magnitude spectra after performing short-time Fourier transform on the audio signals, and the decibel amplitude spectrogram is to take the logarithm on the magnitude spectra, and all the feature parameters are subjected to standard normalization processing.

The extracted feature parameters are transmitted to the edge computing gateway through the communication module, and the edge computing gateway inputs the feature parameters into the trained abnormal sound detection model and the abnormal sound positioning model to detect and locate the abnormal sounds. Abnormal sounds include swine cough, abnormal screams caused by fighting behavior and pain.

The abnormal sound detection model and the abnormal sound positioning model in this embodiment is shown in FIG. 2. The model is divided into two parts, one for abnormal sound detection and the other for abnormal sound positioning. FIG. 2 only shows the processing flow of one channel of signals, and the processing flow of other channel of signals is consistent with this flow. Finally, the model carries out ensemble learning on the output of each channel of signals, and obtains the classification result and the position prediction result. The abnormal sound detection model and the abnormal sound positioning model is composed of depth feature extraction layer, two BiLSTM layers, a full connection layer and an activation layer. The depth feature extraction layer includes three convolution modules (ConvBlock), and each convolution module includes a convolution layer, a batch normalization layer (BatchNorm), an activation function (ReLu), a maximum pooling layer (MaxPooling2D) and a Dropout.

The amplitude spectrogram features extracted from the W, X, Y and Z signals are input into the trained abnormal sound detection model, and ensemble learning is performed on the multi-channel prediction result to obtain the final classification result of the abnormal sound.

The prediction result of abnormal sound is used as a mask to judge whether the abnormal sound is activated or not. If the abnormal sound is in the activated state, the decibel amplitude spectrogram and phase spectrogram features extracted from W, X, Y and Z signals are further input into the trained positioning model, and the multi-channel prediction result is subjected to average ensemble learning to predict the position of abnormal sound.

In the abnormal sound detection model, sigmoid activation function is used, and binary cross entropy is used as loss function. In the positioning model, linear activation function is used, and average absolute error is used as loss function.

In this embodiment, the construction method of the training set for training the abnormal sound detection model and the abnormal sound positioning model is as follows:

firstly, different sound signals, including swine cough, abnormal swine screams and other sound signals except background noise, are collected in different large-scale pigsties by using a recording pen, and the number of the sound signals is not less than 100;

secondly, the impulse response in the actual environment is collected, the empty actual pigsty or laboratory environment is selected, and the pseudorandom sequence is sent by using the recording pen as the point sound source, and the pseudorandom sequence is generated by the M sequence; when the microphone array is used to collect data, the received signal should be ensured to be above 30 dB, and the position distribution of the point sound source is as follows: the position of the direction angle is changed in the range of 0° to 360° with a step of 10°, the position of the pitch angle is changed in the range of −70 to 70° with a step of 10°, and the distance between the point source and the microphone array is changed in the range of 1 meter to 5 meters, and correlation operation is performed on the received pseudorandom sequence and sending sequence to obtain impulse response in real environment;

thirdly, the environmental noises in different real pigsties are collected by using a recording pen, and the environmental noises do not include the swine cough, abnormal screams and other sounds in pigsty except the background noise, and the environmental noises are collected at least three times in different time periods within 24 hours, and each collection time is not less than 20 minutes;

finally, the collected sound signals of pigsties, impulse response and environmental noises are synthesized, and convolution operation is performed on different sound signals of pigsties with different impulse responses to obtain signals with multiplicative interference; then, noise signals with different signal-to-noise ratios are obtained by adding noises with different energies to the convolved signals, and the signals are used as training sets to train the abnormal sound detection model and the abnormal sound positioning model.

The edge computing gateway sends the results to the cloud server, and the cloud server performs predicting and warning against the received data according to the established early warning model of swine abnormal state. The early warning model of swine abnormal state is described as follows:

according to cough and abnormal screams, abnormal states are divided into respiratory diseases and biting fights; according to the prediction results, the frequencies of different abnormal sounds are calculated; the frequency calculation method is the average number of abnormal sounds produced by each swine every 24 hours. The warning information is marked as green when the frequency is less than or equal to 30 times; when the frequency is greater than 30 times and less than or equal to 60 times, the mark is orange; and when the frequency is greater than 60 times, the mark is red. Green means no abnormality, orange means slight abnormality, and red means severe abnormality.

The cloud server sends the early warning information to the mobile phone or computer client, and the early warning information includes the current green, orange and red early warning states, the frequencies of abnormal sounds and the positioning information of abnormal swines.

The above is only the preferred embodiment of this application, but the protection scope of this application is not limited to this. Any change or replacement that may be easily thought of by a person familiar with this technical field within the technical scope disclosed in this application should be covered by this application. Therefore, the protection scope of this application should be based on the protection scope of the claims.

What is claimed is:

1. A method for monitoring abnormal state of swines based on edge computing, comprising following steps:

collecting and preprocessing audio information through a microphone array; wherein the audio information is a first-order ambisonics signal, comprising omnidirectional signals, X-direction signals, Y-direction signals and Z-direction signals;

performing feature extraction on preprocessed audio information to obtain feature parameters, and performing standard normalization processing on the feature parameters; wherein the feature parameters comprise amplitude spectrogram, decibel amplitude spectrogram and phase spectrogram;

constructing an abnormal sound detection model and an abnormal sound positioning model, constructing a training set, training the abnormal sound detection model and the abnormal sound positioning model based on the training set, and obtaining a classification result and a positioning result of an abnormal sound based on processed feature parameters, the abnormal sound detection model and the abnormal sound positioning model;

wherein a training process of the abnormal sound detection model and the abnormal sound positioning model comprises:

collecting clear different sound signals in different pigsties with no superposition of other sound;

sending pseudorandom sequences by point sound source in different pigsty scenes, and receiving the pseudorandom sequences by microphones, and performing correlation operation on the pseudorandom sequences at a receiving end and a sending end to obtain impulse response in a corresponding scene;

collecting environmental noises in the different pigsties, wherein the environmental noises refer to background noises; and after performing convolution operation on different sound signals and different impulse responses, superimposing the background noises with different energies to obtain a noisy signal set comprising multiple signal-to-noise ratios, and using the noisy signal set as the training set, and training the abnormal sound detection model and the abnormal sound positioning model based on the training set;

a process of obtaining the classification result and the positioning result of the abnormal sound comprises:

inputting the amplitude spectrogram into the abnormal sound detection model to obtain a multi-channel classification result, and performing ensemble learning on the multi-channel classification result to obtain the classification result of the abnormal sound; and judging whether the abnormal sound is in an active state by using the classification result as a mask, and if the abnormal sound is in the active state, inputting the decibel amplitude spectrogram and the phase spectrogram into the abnormal sound positioning model to obtain a multi-channel prediction result, and performing ensemble learning on the multi-channel pre-prediction result to obtain the positioning result of the abnormal sound; and constructing an early warning model of swine abnormal state, obtaining the abnormal state based on the classification result and the early warning model of the swine abnormal state, counting frequencies of different abnormal states, generating early warning information based on the frequencies and the positioning result, and sending the early warning information to a client, so as to realize monitoring of the swine abnormal state.

2. The method for monitoring the abnormal state of the swines based on the edge computing according to claim 1, wherein a preprocessing process comprises: performing amplification processing on the audio information, truncating and caching audio information after the amplification processing to obtain cached data, and performing filtering and denoising processing on the cached data.

3. The method for monitoring the abnormal state of the swines based on the edge computing according to claim 1, wherein the abnormal sound detection model uses sigmoid activation function, binary cross entropy as loss function, the abnormal sound positioning model uses linear activation function and average absolute error as loss function.

4. A system for monitoring abnormal state of swines based on edge computing, comprising:

a data acquisition and processing module, an edge computing gateway, a cloud server and a client;

wherein the data acquisition and processing module comprises a microphone array, a digital signal processing module, a power amplification module, a power supply module and a communication module;

the data acquisition and processing module is used for collecting and preprocessing audio information through the microphone array, wherein the audio information is a first-order ambisonics signal, comprising omnidirectional signals, X-direction signals, Y-direction signals and Z-direction signals;

the edge computing gateway is used for performing feature extraction on preprocessed audio information to obtain feature parameters, and performing standard normalization processing on the feature parameters, wherein the feature parameters comprise amplitude spectrogram, decibel amplitude spectrogram and phase spectrogram;

the edge computing gateway is further used for constructing an abnormal sound detection model and an abnormal sound positioning model, constructing a training set, training the abnormal sound detection model and the abnormal sound positioning model based on the training set, and obtaining a classification result and a positioning result of an abnormal sound based on processed feature parameters, the abnormal sound detection model and the abnormal sound positioning model;

wherein the training set is constructed by collecting clear different sound signals in different pigsties with no superposition of other sound; sending pseudorandom sequences by point sound source in different pigsty scenes, and receiving the pseudorandom sequences by the microphone array, and performing correlation operation on the pseudorandom sequences at a receiving end and a sending end to obtain impulse response in a corresponding scene; collecting environmental noises in the different pigsties, wherein the environmental noises refer to background noises; and after performing convolution operation on different sound signals and different impulse responses, superimposing the background noises with different energies to obtain a noisy signal set comprising multiple signal-to-noise ratios, and using the noisy signal set as the training set, and training the abnormal sound detection model and the abnormal sound positioning model based on the training set;

wherein the edge computing gateway is further used for inputting the amplitude spectrogram into the abnormal sound detection model to obtain a multi-channel classification result, and performing ensemble learning on the multi-channel classification result to obtain the classification result of the abnormal sound; and judging whether the abnormal sound is in an active state by using the classification result as a mask, and if the abnormal sound is in the active state, inputting the decibel amplitude spectrogram and the phase spectrogram into the abnormal sound positioning model to obtain a multi-channel prediction result, and performing ensemble learning on the multi-channel pre-prediction result to obtain the positioning result of the abnormal sound; and the cloud server is used for constructing an early warning model of swine abnormal state, obtaining early warning information based on the multi-channel classification results and the early warning model of the swine abnormal state, and transmitting the early warning information to the client, counting frequencies of different abnormal states, generating early warning information based on the frequencies and the positioning result, and transmitting the early warning information to a client, so as to realize monitoring of the swine abnormal state.

5. The system for monitoring the abnormal state of the swines based on the edge computing according to claim 4, wherein the microphone array comprises a plurality of directional microphones, a number of the microphones is not less than four, and the microphones are used for collecting audio data, wherein the audio data comprises a multi-channel synchronous audio signal, and collected multi-channel audio signal is encoded and converted into a first-order ambisonics signal;

the power amplification module is used for performing amplification processing on the audio data;

the digital signal processing module adopts a field programmable gate array (FPGA) module, used for extracting feature parameters after the amplification processing on the audio data and transmitting the feature parameters to the edge computing gateway through the communication module; and the power supply module is used for supplying power to the microphone array, the digital signal processing module, the power amplification module and the communication module.

6. The system for monitoring the abnormal state of the swines based on the edge computing according to claim 4, wherein the edge computing gateway comprises an abnormal sound detection model and an abnormal sound positioning model, both of the abnormal sound detection model and the abnormal sound positioning model comprise a depth feature extraction layer, a plurality of BiLSTM or BiGRU layers, a full connection layer and an activation layer.

7. The system for monitoring the abnormal state of the swines based on the edge computing according to claim 6, wherein the depth feature extraction layer comprises a plurality of convolution layers, batch normalization layers, activation function ReLu, pooling layers and Dropout.

8. The system for monitoring the abnormal state of the swines based on the edge computing according to claim 4, wherein the early warning information obtained by the early warning model of the swine abnormal state comprises several early warning states, frequencies of abnormal sounds and position information of the abnormal sounds.

* * * * *